US00PP13849P29

(12) United States Plant Patent
Mikaelian

(10) Patent No.: US PP13,849 P2
(45) Date of Patent: May 27, 2003

(54) NECTARINE TREE NAMED 'LARRY'S RED'

(76) Inventor: Michael Mikaelian, 10368 Ave. 400, Dinuba, CA (US) 93618

( * ) Notice: Subject to any disclaimer, the term of this patent is extended or adjusted under 35 U.S.C. 154(b) by 0 days.

(21) Appl. No.: 10/013,750

(22) Filed: Dec. 7, 2001

(51) Int. Cl.[7] ..... A01H 5/00
(52) U.S. Cl. ..... Plt./190
(58) Field of Search ..... Plt./188–193

(56) References Cited

U.S. PATENT DOCUMENTS

PP6,363 P 11/1988 Bradford

*Primary Examiner*—Bruce R. Campell
*Assistant Examiner*—Susan B. McCormick
(74) *Attorney, Agent, or Firm*—Mark D. Miller

(57) ABSTRACT

A new and distinct variety of nectarine tree which is characterized by producing a semi clingstone fruit with a red blush coloration and is ripe for commercial marketing and shipment September 9–15 in the San Joaquin Valley of Central California. The new variety is clearly similar to the 'August Red' nectarine (U.S. Plant Pat. No. 6,363) from which it is a sport but from which it is distinguishable by fruit ripening 4 to 5 weeks after the fruit of the 'August Red' nectarine tree and the fruit being somewhat larger in size than that of the 'August Red' nectarine tree. The fruit of this instant variety has a very good flavor compared to the fruit of the 'August Red' nectarine tree.

1 Drawing Sheet

*Prunus persica* var *nectarina*

BACKGROUND OF THE NEW VARIETY

The present invention relates to a new and distinct variety of nectarine tree which will hereinafter be denominated varietally as the 'Larry's Red' nectarine tree which produces semi clingstone fruit which can mature for commercial harvest and shipment approximately September 9th–15th, four to five weeks after the 'August Red' nectarine in the San Joaquin Valley of Central California. This is a fresh market nectarine with a very good red blush in coloration and a larger fruit than the 'August Red'.

In the development of new commercial variations of fruit trees, premium is frequently placed on those varieties that possess good size, skin color (blush), good flavor, good holding and shipping capabilities as well as a niche or specific time unique for this fruit. The nectarine tree of this invention appears to be a promising candidate and wide acceptance in the fresh market is anticipated.

ORIGIN AND ASEXUAL REPRODUCTION OF THE NEW VARIETY

The new variety was asexually reproduced by the inventor's representative in the dormant season of 1999–2000 by bud grafting on Nemaguard rootstock.

SUMMARY OF THE NEW VARIETY

The 'Larry's Red' nectarine is characterized by producing a semi clingstone fruit with a good red blush coloration, ripe for commercial harvest and shipment approximately September 8 to 15. The new variety is closely similar to the 'August Red' nectarine tree (U.S. Plant Pat. No. 6,363) of which it is a bud sport, but is distinguishable from it in that the fruit ripens four to five weeks later than the fruit of the 'August Red' nectarine tree and the fruit is appreciably larger in size than that of the 'August Red' nectarine tree as well as producing a very good flavor.

BRIEF DESCRIPTION OF THE DRAWING

The accompanying drawing is a color photograph showing fruit of the new variety displaying a bottom view showing the apex and sutures thereof, a second view displaying the top with the stem cavity, a third view displaying a side view with the ventral surface thereof, a fourth view of the shape of the basal and apical ends of the fruit, a fifth view sectional to show the flesh, the pit cavity and the pit (stone), and the last view of the foliage of the new variety of nectarine tree.

DETAILED DESCRIPTION

Referring more specifically to the horticultural details of the new and distinct variety of nectarine tree, the following details have been observed under the ecological conditions prevailing at the orchard of origin which is located near Cutler, Calif. in the San Joaquin Valley of Central California. All major color designations are by reference to the dictionary of color by Maerz & Paul, First Edition, 1930. Common colors are also commonly employed.

Tree

Generally the amount of top growth is about the same as that produced by the parent tree 'August Red' nectarine.

Size: Medium (approximately 12–15 feet in height, with a spread of approximately 10–12 feet, depending upon cultural practices, fertilization, pruning, soil conditions, climate, watering, temperature, girdling and available space)

*Circumference of trunk.*—28 inches at 4 inches above ground.

Shape: Upright and slightly spreading

Trunk: With rough bark.

*Color.*—Mauve Taupe (7-C-8).

*Lenticels.*—Number moderate.

*Size.*—Medium.

Branches: Medium to large.
*Circumference.*—At 2 feet above ground — 13¾–14¾ inches.
*Texture.*—Mature branch — smooth — color Piquant Green (20-K-6).
*Color.*—Mature branch — Haemotite Red (7-H-3).
*Lenticels.*—Numerous.

Leaves

Size: Large.
*Length.*—150–180 mm — Average 167.5 mm (6.59 inches).
*Width.*—39–55 mm — Average 48.33 mm (1.90 inches).
Form: Lanceolote, leaf tip average acuminate.
Arrangement: Opposite.
Color code:
*Upwardly disposed surface* (*top*).—Perido (22-L-6).
*Downwardly disposed surface* (*bottom*).—Near Fern Green (21-I-7).
Marginal form: Serrulate.
Glands: Reniform 2–4 at base of leaf — green.
Vein: Russet Green (20-K-1).
Venation pattern: Pinnate.
Petioles:
*Length.*—11–15 mm (0.43–0.59 inch).
*Width.*—1½–2½ mm (0.06–0.098 inch).
*Color.*—Russet Green (20-K-1).
Peduncle:
*Length.*—10–12 mm (0.039–0.047 inch).
*Width.*—4–5 mm (0.0057–0.0197) new.
Stipules: 2 double.
*Color.*—Mirador Argentina Art Brown (8-L-6).
*Size.*—Small, 3 mm (0.12 inch).

Flowers

Flower bud: Hardy under climatic conditions prevalent in the San Joaquin Valley of Central California.
*Bud size.*—Average — 8 mm wide (0.315 inch), 10 mm long (0.294 inch).
*Form.*—Conic and closely attached to fruiting wood.
*Bud color.*—Indian Red (7-L-6).
Flowers: Generally showy type, opposite and highly fragrant.
*Date of bloom 30–40%.*—February 28.
*Size.*—Generally large, 30 mm average (1.18 inch).
Petals:
*Size.*—Medium to large, five in number.
*Length.*—Average 15 mm (0.59 inch).
*Width.*—12–13 mm (0.472–0.512 inch).
*Color.*—Petals are light pink (1-H-2), with the margins on edges darker pink and on petal claw.
*Abaxial surface.*—Flat, slightly pubescent, with dark pink (2-H-2) color.
Petal claws: Broadly truncate.
*Width.*—1.5 mm (0.059 inch).
*Length.*—1–2 mm (0.039–0.078 inch).
Petal margins: Moderately undulate with generally rounded apex.
Flower pedicel: Short.
*Length.*—Average 2 mm (0.0787 inch).
*Width.*—1.5 mm (0.062 inch).
Calyx: 5 Sepals, slightly pubescent surface.
*Color.*—Indian Red (7-L-6).
*Size.*—4–5 mm wide (0.158–0.197 inch), 5 mm long (0.197 inch).
Anthers: Small.
*Color.*—Pimuline Y (10-L-5).
Pollen: Abundant.
Stamens: 30–35.
*Length.*—10–12 mm (0.394–0.472 inch).
*Filament.*—Color — Light Pink (1-G-2).
Pistil: One.
*Length.*—Average 19 mm (0.748 inch).
*Color.*—Light Green (17-K-2).

Fruit

Size: Maturity Sep. 8–15$^{th}$ (13° Brix).
Average diameter — axial plane: 62–70 mm, average 2.66 inches.
*Average transverse — suture plane.*—62–69 mm, average 2.62 inches.
*Average transverse at right angles to suture plane.*—65–67 mm, average 2.51 inches.
Form: Uniform; slightly asymmetrical.
Suture: Pronounced but shallow.
Ventral surface: Slightly uneven.
Stem cavity: Somewhat shallow.
*Width.*—15–18 mm (0.594–0.709 inch).
*Depth.*—Average 6 mm (0.236 inch).
*Length.*—20–21 mm (0.787–0.827 inch).
Stem: Short, 6 mm (0.236 inch).
Caliper: Average 3 mm (0.118 inch).
Apex: Round.
Pistil point: Retuse.
Base: Slightly rounded.
Skin: Normal for nectarines and similar to parent 'August Red'.
Texture: Firm and smooth.
Color code:
*Blush color.*—Pomegranate (6-L-3) over majority of fruit surface.
*Ground color.*—Empire Y (9-K-3).
Flesh color:
*Near the skin.*—Light Stone (12-J-5).
*Near pit well reddening.*—Amaranth Pink (53-L-3).
Color of surface near pit cavity: Amaranth Pink (53-L-3).
Color of pit cavity well: Rhododendron (54-J-6).
Juice production: Good.
Flavor: Sweet.
Aroma: Good.
Texture: Firm.
Fibers:
*Number.*—Many.
*Texture.*—Stringy.
Ripens: Even.
Eating quality: Good.
Average pressure test: 12 lbs.
Holding capacity (storage): Very good.

Stone

Free or cling: Semi clingstone.
Fibers: Adhering to stone.
*Numbers.*—Many.
*Length.*—Long, average 13 mm (0.51 inch).
Stone size:
*Length.*—30–32 mm (1.18–1.26 inches).
*Width.*—26 mm (1.02 inches).
*Thickness.*—13.3 mm (0.51 inch).
Form: Generally ovate.
Apex: Rounded with blunt point.
Color: When dry, Reddish Brown (55-H-J-6).

Base: Slightly flattened.
Sides: Generally unequal.
Hilium: Scar small and oval in shape.
Ridges: Grooved, ventral edge, relatively narrows from base to apex.
Tendency to split: Not known.
Use: Fresh market.

Although the new variety of nectarine tree possesses the above described characteristics as a result of growing conditions prevailing near Cutler, Calif. in the San Joaquin Central Valley, it is to be understood that variations of the usual magnitude may occur as a result of changes in growing conditions and cultural practices (irrigation, fertilizers, pruning, pest control was well as climate).

Having thus described and illustrated my new variety of nectarine tree, what I claim as new and desire to be secured by Plant Letters Patent is:

1. A new and distinct variety of nectarine tree substantially as illustrated and described which is remotely similar to the 'August Red' nectarine tree (U.S. Plant Pat. No. 6,363) from which it is a sport but from which it is distinguished by producing a later maturing fruit with good size, exterior coloration and eating quality which matures for commercial harvesting and shipment September 8–15, or about 3–4 weeks after the fruit of 'August Red'.

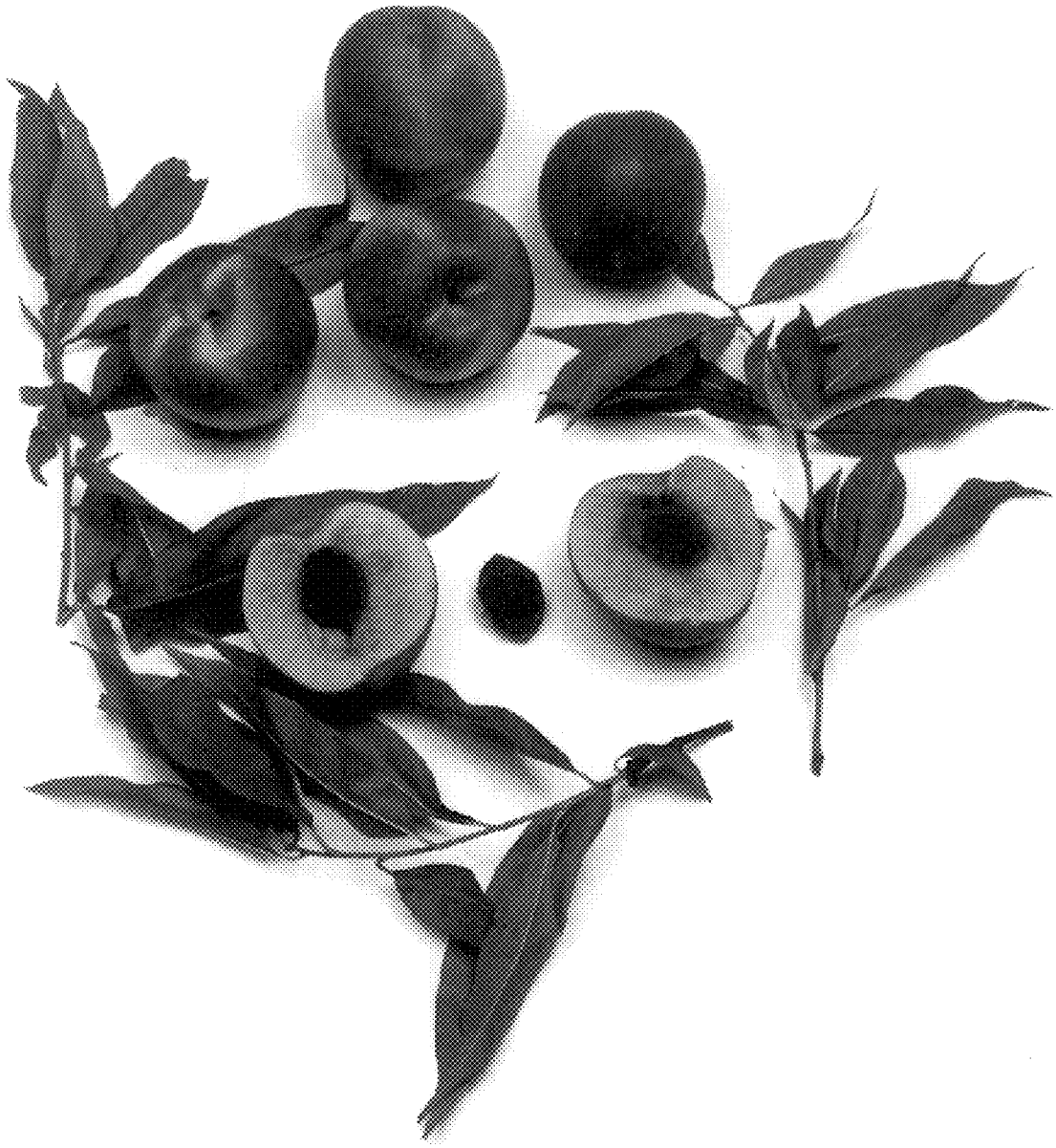

* * * * *